(12) United States Patent
Hofstedt

(10) Patent No.: US 10,379,031 B2
(45) Date of Patent: Aug. 13, 2019

(54) METHOD FOR MEASURING SOAP CONTENT IN BLACK LIQUOR AND AN ANALYTICAL CONTAINER

(71) Applicant: Anders Goran Hofstedt, Linkoping (SE)

(72) Inventor: Anders Goran Hofstedt, Linkoping (SE)

( * ) Notice: Subject to any disclaimer, the term of this patent is extended or adjusted under 35 U.S.C. 154(b) by 324 days.

(21) Appl. No.: 14/778,373

(22) PCT Filed: Mar. 19, 2014

(86) PCT No.: PCT/SE2014/050329
§ 371 (c)(1),
(2) Date: Sep. 18, 2015

(87) PCT Pub. No.: WO2014/148993
PCT Pub. Date: Sep. 25, 2014

(65) Prior Publication Data
US 2016/0146720 A1  May 26, 2016

(30) Foreign Application Priority Data

Mar. 20, 2013 (SE) ...................................... 1300211

(51) Int. Cl.
*D21C 11/00* (2006.01)
*G01N 19/00* (2006.01)
*G01N 33/00* (2006.01)

(52) U.S. Cl.
CPC ............ *G01N 19/00* (2013.01); *D21C 11/00* (2013.01); *D21C 11/0007* (2013.01); *G01N 33/00* (2013.01)

(58) Field of Classification Search
CPC ............ B01D 17/0208; B01D 17/0214; B01D 21/0012; B01D 21/009; B01D 21/10;
(Continued)

(56) References Cited

U.S. PATENT DOCUMENTS 3,326,743 A * 6/1967 Bryce ....................... D21C 7/08
162/19
3,712,118 A * 1/1973 Mason ............... G01N 33/2823
210/634
(Continued)

FOREIGN PATENT DOCUMENTS

CL    2015002777 A1   7/2016
CN        1130254 A    9/1996
(Continued)

OTHER PUBLICATIONS

International Search Report, dated Jun. 12, 2014, from corresponding PCT Application.
(Continued)

*Primary Examiner* — Randy W Gibson
*Assistant Examiner* — Gedeon M Kidanu
(74) *Attorney, Agent, or Firm* — Young & Thompson

(57) ABSTRACT

An analytical method and container for measuring the soap content in black liquor. The method includes: a first step where a defined amount of black liquor is arranged in the container, a second step where the black liquor is centrifuged and a soap concentrate is gathered in the upper part of the container, a third step where the amount of soap concentrate is determined, and a fourth step where the soap content is calculated. By centrifuging the black liquor soap concentrated with a soap content of 58-62% is obtained, which enables measurement of the dry matter with an accuracy of ±2% within a very short time period. The container includes a neck with scale marks and a lower part. In one embodiment, the analytical method includes a fifth step where a modification of the calculated soap content is made with consideration to the density of the black liquor.

4 Claims, 3 Drawing Sheets

(58) Field of Classification Search
CPC ............... B01D 21/2405; B01D 21/2444; B01D 17/00; B01D 17/12; B01D 21/0042; B01D 21/2416; B01D 21/2427; B01D 21/34; B01D 2221/02; D21C 11/00; D21C 11/0007; D21C 11/0042; G01N 19/00; G01N 33/00; G06F 2003/0697; G06F 3/0601

See application file for complete search history.

(56) References Cited

U.S. PATENT DOCUMENTS

| | | | |
|---|---|---|---|
| 3,804,261 A * | 4/1974 | Whelan | B01D 17/0208 210/519 |
| 4,085,000 A | 4/1978 | Otrhalek et al. | |
| 4,208,286 A * | 6/1980 | Kauppi | B01D 17/0214 162/16 |
| 4,557,899 A * | 12/1985 | Schoonover | G01N 33/2847 422/401 |
| 5,220,172 A | 6/1993 | Berthold et al. | |
| 5,229,295 A * | 7/1993 | Travis | G01N 31/222 436/166 |
| 5,308,504 A * | 5/1994 | Keyes | D21C 11/0007 162/238 |
| 5,575,950 A * | 11/1996 | Steelman | B01D 19/0404 516/118 |
| 5,843,336 A * | 12/1998 | Steelman | B01D 19/0404 162/158 |
| 6,165,316 A * | 12/2000 | Iivonen | D21C 11/0007 162/16 |
| 6,409,808 B1 * | 6/2002 | Chamberlain | B01D 19/0057 210/188 |
| 6,582,601 B1 * | 6/2003 | Heinamaki | B01D 17/0214 210/532.1 |
| 7,105,076 B2 * | 9/2006 | Stromberg | D21C 7/06 162/17 |
| 8,009,277 B2 * | 8/2011 | Chai | G01N 21/33 162/263 |
| 2006/0185421 A1 * | 8/2006 | Walker | G01N 9/04 73/32 R |
| 2012/0296066 A1 * | 11/2012 | Hofstedt | C11B 13/005 530/205 |

FOREIGN PATENT DOCUMENTS

| | | |
|---|---|---|
| CN | 202010560 U | 10/2011 |
| CN | 202485764 U | 10/2012 |
| WO | 9742371 A1 | 11/1997 |
| WO | 2005/059242 A1 | 6/2005 |
| WO | WO 2005059242 A1 * | 6/2005 ............ D21C 11/00 |
| WO | 2011081587 A1 | 7/2011 |
| WO | 2014148996 A1 | 9/2014 |

OTHER PUBLICATIONS

Oct. 28, 2016, EP communication issued for related EP application No. 14771054.5.

Mar. 23, 2017, CL communication issued for related CL application No. 201502777.

* cited by examiner

METHOD FOR MEASURING SOAP CONTENT IN BLACK LIQUOR AND AN ANALYTICAL CONTAINER

The present invention relates to an analytical method for measuring the content of soap in black liquor and an analytical container suitable for use in such a method according to the initial part of the independent claims.

BACKGROUND OF THE INVENTION

In the kraft method, the wood raw material is boiled with white liquor so that the lignin in the wood is dissolved and the cellulose fiber is exposed. The white liquor becomes black during boiling and is then referred to as black liquor. The cellulose fiber is filtered from the black liquor and then takes its own path in the plant, which is usually referred to as the fiber line. The black liquor is pumped away for recycling of chemicals and the production of new white liquor.

The wood raw material comprises approximately 1-4% extractive matter, primarily fatty acids, resin acids and neutral compounds, of which resin acids is only present in conifers. The fatty acids and the resin acids are saponified during boiling with the liquor and forms what is, within the mill, usually referred to as soap. Since the neutral compounds are hydrophobic they also end up in the soap phase. The soap must be separated from the black liquor, otherwise there will be problems during evaporation and possibly also in the recovery boiler, so it is of great importance to know the soap content of the black liquor during the different steps on the way to the recovery boiler. Current analytical methods depends on chemistry and takes long time to carry out, typically 2-4 hours, which results in that the estimated soap content at any time point refers to the actual soap content two to four hours earlier, unless the process is stopped during such a time period, which off course is unsuitable.

A purpose of the current invention is to provide a method for analysis for the measurement of soap content in black liquor which provides results faster than the currently known methods.

Another purpose of the invention is to provide an analytical container which is suitable to use with such an analytical method for the measurement of soap content in black liquor.

These and other goals are achieved by an analytical method and an analytical container.

SUMMARY OF THE INVENTION

The invention concerns an analytical method for at least measuring the content of non-dissolved soap in black liquor. The analytical method comprises a first step where a well-defined amount of black liquor is arranged in cylindrically symmetrical analytical container, a second step where the black liquor in the analytical container is centrifuged and a soap concentrate is gathered in the upper part of the analytical container, a third step where the amount of soap concentrate is determined, and a fourth step where the soap content is determined to be in the interval of 58-62% of the amount of soap concentrate. By centrifuging the black liquor, a soap concentrate with a soap content of 58-62% is obtained, which allows the determination of soap content with an accuracy of ±2% in a very short time. In a simplified version the soap content can be considered to be 60% of the quantity of soap concentrate.

In a preferred embodiment of the invention, the analytical method comprises a fifth step, where the determined soap content is modified based on the density of the black liquor, which is influenced by, among other things, the temperature of the black liquor.

In another preferred embodiment of the invention, the cylindrically symmetrical analytical container comprises a neck with scale marks and a lower part. The well-defined amount of black liquor is defined by filling the analytical container to the uppermost scale mark, while the amount of soap concentrate is determined by the lower boundary surface of the soap concentrate being measured by use of the scale marks.

The invention in addition comprises an analytical container for use in such a method.

DESCRIPTION OF PREFERRED EMBODIMENTS

The analytical method according to the invention is based on the centrifugation of the black liquor so that a concentrate with a high soap content is separated from the remaining black liquor. After boiling there is present approximately 25-45 g extractive matter in the black liquor, per kg of dry matter of the black liquor. The soap content remains constant even though the percentage can increase with the increasing concentration of the black liquor during the evaporation steps. When the soap is separated from the black liquor the soap will always comprise a part of black liquor, even though it is not visible to the eye. Therefore it is of great importance to know the proportion of extractive matter in the soap, in order to convert volume of separated soap into soap content in the black liquor. Measurements have shown that the extractive matter content in centrifuged soap is from 58-62%. In the analytical method according to the invention it can be assumed that the extractive matter content in centrifuged soap is 60% with a deviation of only ±2%. Thus, when the black liquor has been centrifuged the actual amount of soap can be determined from the amount of soap concentrate.

If, in addition, the dry matter content of the black liquor when the sample is taken is known, the extraction matter content per kg dry matter can also be determined, if in addition, the densities of the black liquor and the separated soap is known. The dry matter content of the black liquor is known in all mills, and if not, can be rapidly determined with the use of a balance simultaneously with the centrifugation.

As an example of calculation of the concentration of extraction matter it is here assumed that the dry matter content of the black liquor is 21%. At 90° C. the density is 1.093. For the separated soap the density is approximately 1.023. If the centrifugation test with an analytical container of 1 liter yields that we have 1 volume % of soap in the black liquor, the following values are obtained, using 1000 ml of black liquor as the basis for calculation:

Black liquor 990 ml*1.093=1082 g

Dry matter concentration of black liquor:
    21%*1082=227.23 g

Soap: 10 ml*1.023=10.23 g

Extraction matter: 60%*10.23=6.14 g

Result: 1000*6.14/227.3=27 g extraction matter/kg dry matter of black liquor.

Figure 1:
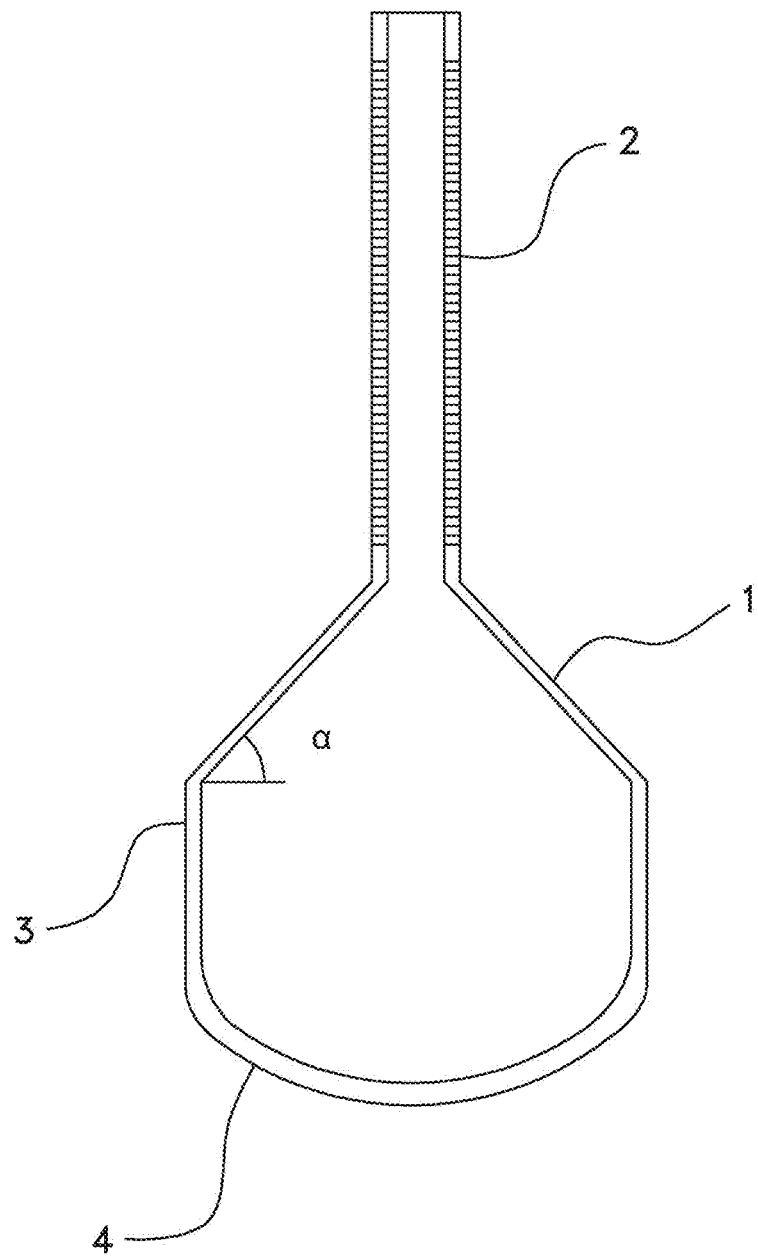
FIG. 1 shows a first embodiment of an analytical container according to the invention.

FIG. 1 shows a first embodiment of an analytical container according to the invention. The analytical container is designed to be centrifuged in order to separate the soap from the black liquor. The analytical container furthermore comprises a lower portion 1 and a neck 2, where both these parts are cylindrically symmetrical and arranged around a common axis of symmetry. The first embodiment is intended for analysis of black liquor with a high concentration of soap, as the volume of the lower portion is relatively small compared to the inner volume of the neck. The lower portion has a cylindrical mid part 3, which is connected downward to bottom part 4 which is shaped as a part of a sphere. The lower portion connects upwards to a part shaped like a truncated cone. The angle α between the cylindrical mid part 3 and the cone-shaped part is 48°. The top of the truncated cone connects to the neck 2. The neck comprises a cylindrical cavity with a uniform cross section throughout the neck. There are scale marks on the neck, from close to the top of the neck to close to the bottom part of the neck.

Figure 2:
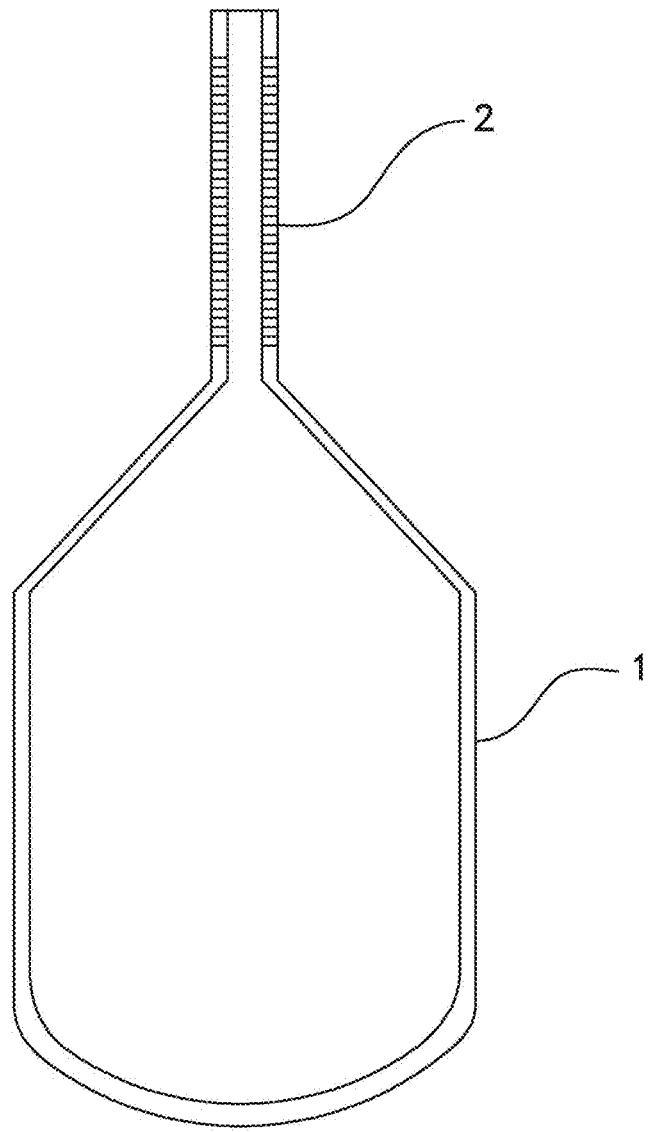
FIG. 2 shows a second embodiment of an analytical container according to the invention.

FIG. 2 shows a second embodiment of an analytical container according to the invention. The analytical container, as in the first embodiment, comprises a larger lower portion 1 and a neck 2. The second embodiment is intended for analysis of black liquor with a lower concentration of soap, by having a lower portion with a relatively smaller volume in relation to the neck than in the first embodiment. Otherwise, the analytical container is arranged in a similar manner as in the first embodiment, where the lower portion has a cylindrical mid part 3, a bottom part 4 and an top part shaped like a truncated cone. As in the first embodiment, the neck comprises a cylindrical cavity with uniform cross section throughout the neck. There are scale marks on the neck, from close to the top of the neck to close to the bottom part of the neck.

Figures 3, 4:
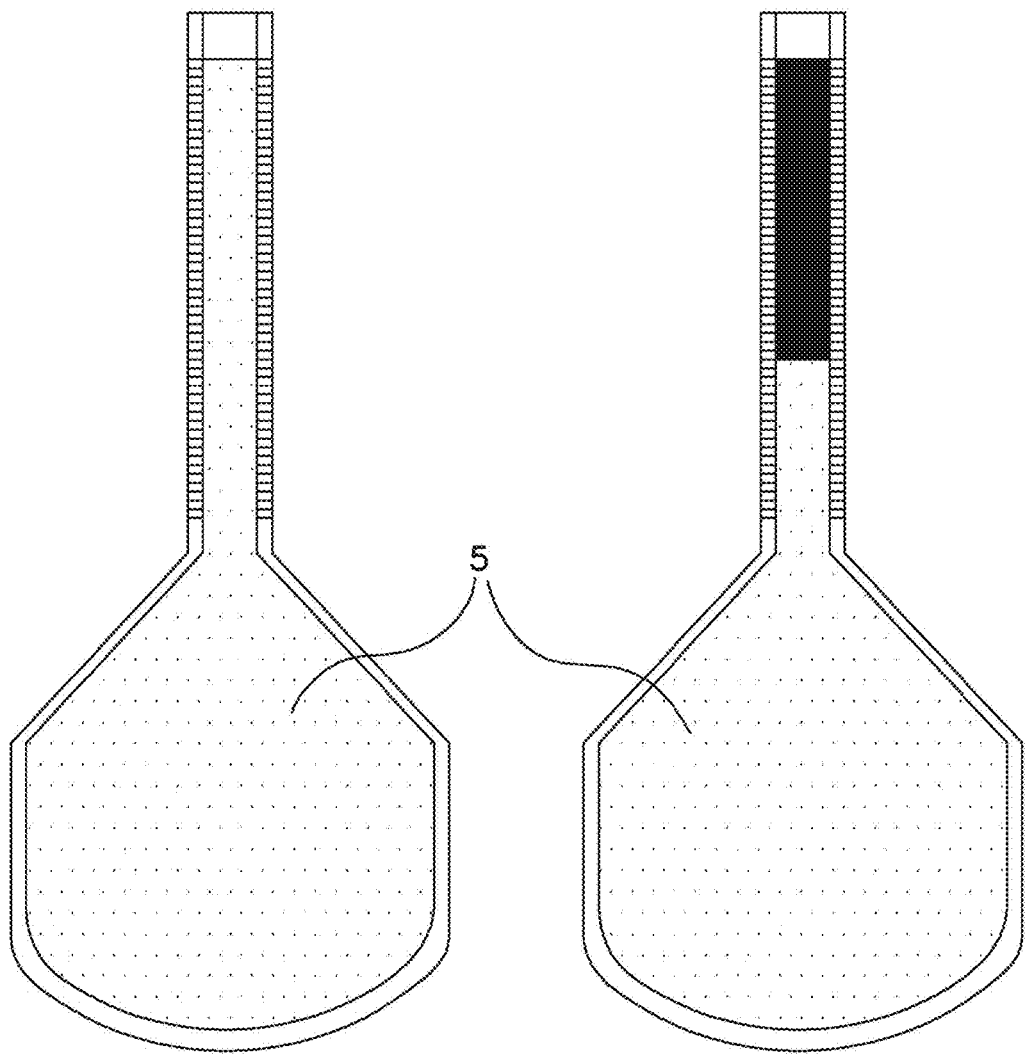
FIG. 3 shows the analytical container according to the first embodiment filled with black liquor.
FIG. 4 shows the analytical container according to the first embodiment where the soap has been separated from the black liquor.

FIG. 3. Shows a container according to the first embodiment filled with black liquor 5. The volume of black liquor filled into the analytical container is such that the surface of the black liquor is level with the uppermost scale mark of the neck of the analytical container.

FIG. 4 shows the container according to the first embodiment where the soap has been separated from the black liquor by centrifugation. The soap has gathered in the neck and floated to the upper part of the neck. Thus, the soap is located from the uppermost scale mark of the analytical container and downwards. The location of the boundary between black liquor and soap in relation to the scale marks indicates the concentration of soap. The concentration of dry matter can be calculated from the value that can read off the scale, with appropriate consideration taken to the temperature-dependent density of the black liquor.

During centrifugation the lighter soap is gathered in the center of the analytical container and then also tends to move upwards, since the soap is lighter than the black liquor. During centrifugation and for a time after centrifugation, the boundary between the soap and the black liquor is indistinct. When the liquid has stopped moving the boundary becomes clearer so that a value can easily be read of the scale.

The invention claimed is:

1. An analytical method for measuring a soap content in black liquor, said method comprising:
    a first step of arranging a well-defined amount of black liquor in a cylindrically symmetrical analytical container comprising a neck with scale marks and a lower portion;
    a second step of centrifuging the black liquor in the analytical container, and gathering a soap concentrate in an upper part of the analytical container;
    a third step of determining an amount of soap concentrate is by a lower boundary of the soap concentrate being measured with the scale marks;
    a fourth step of calculating the soap content, wherein the soap content is determined as 60% of the amount of the soap concentrate; and
    after said fourth step, a step of determining an extraction matter content in the black liquor based on a known dry matter content of the black liquor.

2. The analytical method according to claim 1, further comprising a fifth step, after said fourth step and before said step of determining an extraction matter content, said fifth step comprising modifying the soap content based on the density of the black liquor.

3. The analytical method according to claim 1, wherein a defined amount of black liquor is defined by filling the analytical container to an uppermost scale mark.

4. The analytical method according to claim 1 wherein, in a preceding step, said amount of black liquor is taken from a larger amount of black liquor and is filled into the analytical container for measurement of the soap content in the black liquor in question.

* * * * *